(12) United States Patent
Ward

(10) Patent No.: US 6,379,949 B1
(45) Date of Patent: Apr. 30, 2002

(54) PREFILLED FLEXIBLE CONTAINERS FOR CULTURING MICROORGANISMS

(75) Inventor: N. Robert Ward, Woodinville, WA (US)

(73) Assignee: International BioProducts, Inc., Bothell, WA (US)

( * ) Notice: Subject to any disclaimer, the term of this patent is extended or adjusted under 35 U.S.C. 154(b) by 0 days.

(21) Appl. No.: 09/580,868

(22) Filed: May 30, 2000

Related U.S. Application Data

(62) Division of application No. 09/185,375, filed on Nov. 3, 1998, now Pat. No. 6,146,875, which is a division of application No. 08/850,837, filed on May 2, 1997, now abandoned.

(51) Int. Cl.[7] ............................................... C12M 1/24
(52) U.S. Cl. .................................. 435/304.1; 435/297.5
(58) Field of Search ........................... 435/287.6, 288.1, 435/297.1, 297.5, 304.1; 383/104, 121.1, 9

(56) References Cited

U.S. PATENT DOCUMENTS

| | | | |
|---|---|---|---|
| 3,102,082 A | | 8/1963 | Brewer |
| 3,567,074 A | * | 3/1971 | Brown |
| RE28,969 E | | 9/1976 | Naito |
| 4,027,427 A | * | 6/1977 | Stoller et al. |
| 4,140,162 A | | 2/1979 | Gajewski et al. |
| 4,146,133 A | | 3/1979 | Bogorad et al. |
| 4,186,786 A | | 2/1980 | Kirkpatrick |
| 4,356,954 A | * | 11/1982 | Mojonnier |
| 4,600,104 A | * | 7/1986 | Yanase |
| 4,837,849 A | | 6/1989 | Erickson et al. |
| 4,869,398 A | | 9/1989 | Colvin et al. |
| 4,892,832 A | * | 1/1990 | Omote et al. |
| 4,904,093 A | | 2/1990 | Woods et al. |
| 4,910,147 A | * | 3/1990 | Bacehowski et al. |
| 4,954,124 A | | 9/1990 | Erickson et al. |
| 5,071,760 A | | 12/1991 | Watanabe et al. |
| 5,134,875 A | * | 8/1992 | Jensen et al. |
| 5,143,739 A | | 9/1992 | Bender et al. |
| 5,225,346 A | | 7/1993 | Matsumiya |
| 5,362,642 A | | 11/1994 | Kern |
| 5,458,593 A | | 10/1995 | Macabasco et al. |
| 5,565,015 A | | 10/1996 | Kobayashi |
| 5,787,428 A | * | 7/1998 | Mazzocchi |

OTHER PUBLICATIONS

Miller et al. J. Food Protect. vol. 58(1), pp. 115–119, 1995.
Pelczar et al. Microbiology, pp. 136–137, 1977.
Blankenship et al. J. Food Protect. vol. 46(6), pp. 510–513, 1983 Avstract Enclosed.
Bailey et al. J. Appl. Bacteriol. vol. 51, pp. 409–414, 1981.
Stern et al. J. Food Protect. vol. 55(9), pp. 663–666, 1992.

* cited by examiner

Primary Examiner—William H. Beisner
(74) Attorney, Agent, or Firm—Christensen O'Connor Johnson Kindness PLLC

(57) ABSTRACT

The invention is a prefilled culture medium bag with a gusseted base that is capable of standing in an upright position. The prefilled culture medium bag can be sterilized by irradiation. Or alternatively, the culture medium can be sterilized apart from the bag and subsequently placed inside the bag after the bag has been sterilized. In either case, the end product is a pre-sterilized and prefilled culture medium bag delivered to a laboratory for use. The culture medium bag is self-supporting and takes on the characteristics of a rigid container when filled. The culture medium bag is easy to open and reseal for introduction of a culture sample at the laboratory. After introduction, a sample can be incubated within the culture medium bag.

6 Claims, 6 Drawing Sheets

PREFILLED FLEXIBLE CONTAINERS FOR CULTURING MICROORGANISMS

This application is a divisional of application Ser. No. 09/185,375 (filed Nov. 3, 1998), now U.S. Pat. No. 6,146,875, which is a continuation-in-part of application Ser. No. 08/850,837, filed May 2, 1997, now abandoned.

TECHNICAL FIELD

More particularly, it relates to a prefilled culture medium bag that can be presterilized and delivered to a laboratory ready for the introduction of a culture containing microorganisms therein.

BACKGROUND INFORMATION

Microbiologists incubate samples in sterile liquid culture media to detect and perform tests for pathogenic microorganisms. Salmonella, Listeria, Campylobacter and *E. coli* are some of the typical microorganisms subject to culturing in this manner. Similar kinds of tests are conducted to detect the presence of microorganisms in samples normally expected to be sterile, such as blood, spinal fluid, medical devices, and a wide variety of industrial materials.

Historically, microbiologists prepare sterile liquid culture solutions and buffered diluent solutions (collectively "culture media") in glass or plastic bottles ("rigid containers"). Although rigid containers can be reused, the preparation of culture media in these containers is expensive, labor intensive, and subject to error.

A laboratory that prepares its own culture media typically undertakes a series of steps. First, the container is washed and rinsed to remove any residual substances or chemicals that may inhibit the growth of microorganisms. Then a measured amount of purified water and a powdered culture mix are placed in the container. The water is heated to dissolve the mix in the water and Ph adjustments are made, as necessary. This is followed by sterilizing the container and its contents in an autoclave. The test sample is then introduced into the culture medium after sterilization.

Because the foregoing procedure is labor intensive, many laboratories now prefer to purchase prefilled and presterilized rigid containers, rather than conduct mixing and sterilization themselves. This leaves the laboratory with the task of merely introducing test samples into the containers after they arrive.

Regardless of whether a lab makes and sterilizes its own culture media or purchases prefilled and presterilized containers, rigid containers have been the containers of choice. They can easily withstand the autoclave conditions (121° C., 15 p.s.i., 100% steam) necessary to sterilize liquid culture media.

Glass is particularly advantageous as a container because it allows visual inspection of the culture media before and after a sample is added. Because it is a rigid container, it can be easily moved from place to place. It rests easily on any flat surface and does not require supporting racks or similar structures.

In the prefilled situation, the impermeability of glass extends the shelf life of the culture media by preventing evaporative loss. While plastic is used in many instances because it weighs less than glass and is relatively resistant to breakage, many types of plastics cannot withstand autoclave conditions. The types of plastics which can withstand autoclave conditions are expensive, have reduced clarity, and tend to distort or break after repeated autoclave exposure.

In general, rigid containers are expensive to make (the cost of a cap for capped containers can be as much as 25% of the total cost of the container), heavy to ship, subject to breakage, and contribute to total waste disposal. The breakage and weight problems associated with rigid containers are particularly disadvantageous when they are prefilled and presterilized at one geographic location and then shipped to another location for use.

A further problem with rigid containers is that they do not allow a user to easily mix a sample into the culture media. When mixing is required, the container must be shaken to adequately distribute the sample in the media. If shaking will not work because of sample type, the contents of the container must be transferred to a blender bag which is then placed in a machine having reciprocating paddles that pulverize and mix the sample with the culture media. After mixing, the sample and media must be returned to the rigid container for incubation.

As will become apparent, the present invention solves the above problems and provides a more convenient, less expensive, and better way to culture samples.

SUMMARY OF THE INVENTION

The invention is a prefilled culture medium bag including a closure means and a gusseted base permitting the bag to stand upright when filled.

The invention incorporates the use of a gusseted plastic bag. For definitional purposes, a gusseted bag is one having a gusseted base which allows the bag to stand alone without any external support. In the preferred embodiment, the gusseted bag is comprised of a pair of thin film plastic sheets that lay one on top of the other when the bag is not filled with a culture medium. The lower portion or region of the sheets are connected together and closed to form the gusseted base. The side edges of the sheets are bonded directly to each other without the use of a gusset. The upper portion or region of the sheets may be spread apart in order to fill the bag.

In accordance with one embodiment of the invention, the liquid culture medium is sterilized before it is placed in a presterilized bag. Presterilization of the liquid culture medium is done by placing the medium in an autoclave and subjecting it to sterilization temperatures and pressures. According to what is presently believed to be the preferred embodiment, the bag is presterilized using a separate procedure of irradiation to kill any microorganisms.

The presterilized bag is then filled with the presterilized culture medium in a clean room. Since the bag is gusseted and self-supporting, it stands up by itself when filled and can be moved from place to place like a rigid container.

The prefilled and presterilized bag is then shipped to a lab for incubating a sample (sometimes called "culture sample"). The culture sample is added to the culture medium by opening the bag and subsequently sealing it. Preferably, the bag is designed to have a resealable opening in the form of a "ziplock" closure, although other ways of sealing the bag may work just as well. After sealing, the sample is incubated in accordance with known incubation procedures, according to sample type.

An alternative method of resealing the bag is to use a closure wire instead of a "zip lock" closure. The closure wire is connected to the upper portion of one of the sheets, and the closure wire has a length that exceeds the width of the bag. After the culture medium is added to the bag, the upper portions of the pair of sheets, above the wire closure, are bonded together to form an airtight seal. When the bag arrives at the laboratory for use, the upper portion of the bag is spread open to break the airtight seal, allowing a culture sample to be inserted into the bag. Afterwards, to reseal the bag, the upper portion of the bag is folded or rolled about the closure wire, and then the ends of the closure wire are wrapped around the rolled upper portion, to prevent it from unrolling In an alternative embodiment, the bag and medium are sterilized in the same step by radiation treatment. In this embodiment, a non-sterile culture broth is added to a non-sterile bag and then subjected to radiation treatment by gamma rays or electrons to render the product sterile. This alternative will be further described below.

An advantage of the invention is that it works particularly well in situations where the sample is not easily dissolved in the culture medium. In some cases, in order to obtain a good distribution of the sample, it is necessary to physically stir or beat the mixture. When the above process is used, the solution of medium and sample can be quickly pulverized or kneaded through the walls of the flexible bag, as needed, without transferring bag contents from one container to another. This reduces the risk of introducing unwanted contaminants. As mentioned above, container to container transfer is a drawback in this situation if rigid containers are used.

A second advantage of the invention is that use of a clear, gusseted bag allows visual inspection of the culture medium and sample at any time during the culturing or test process. For example, a user can easily determine whether the contents of a prefilled and sterilized bag have been contaminated at any point in time during shipment or storage. Typically, a prefilled and presterilized bag will be quarantined for a period of time as a manufacturer's test for sterility prior to supplying it to a laboratory. Quarantine will reveal contamination by visual inspection. If the bag passes quarantine, then it is deliverable to the laboratory as a "ready-to-use" unit for incubation purposes. Similarly, after the sample is placed in the bag and incubated, the user can visually inspect it for microorganism growth.

A third and most important advantage of the invention is that it significantly reduces laboratory costs. There is now a significant market relating to supplying labs with prefilled and presterilized culture media in ready-to-use, rigid containers. However, there is no mechanism in place for easy recycling of the containers back to the supplier for reuse. Consequently, the containers tend to be used once and then disposed of by the lab. Not only does this create unnecessary work, but the incremental cost of the container alone is significant relative to what is supplied to the laboratory. Replacing rigid containers with gusseted bags or pouches retains all the existing advantages of rigid containers and provides additional advantages relating to significantly lower costs per container (a cost savings of approximately 20–40% per container) and a reduction in total mass and volume of waste material.

Having briefly summarized the invention, it will become better understood after review of the following description, which is to be taken in conjunction with the drawings.

BRIEF DESCRIPTION OF THE DRAWINGS

In the drawings, like reference numerals and letters refer to like parts throughout the various views unless specifically indicated otherwise, and wherein.

BEST MODE FOR CARRYING OUT THE INVENTION

Figure 1:
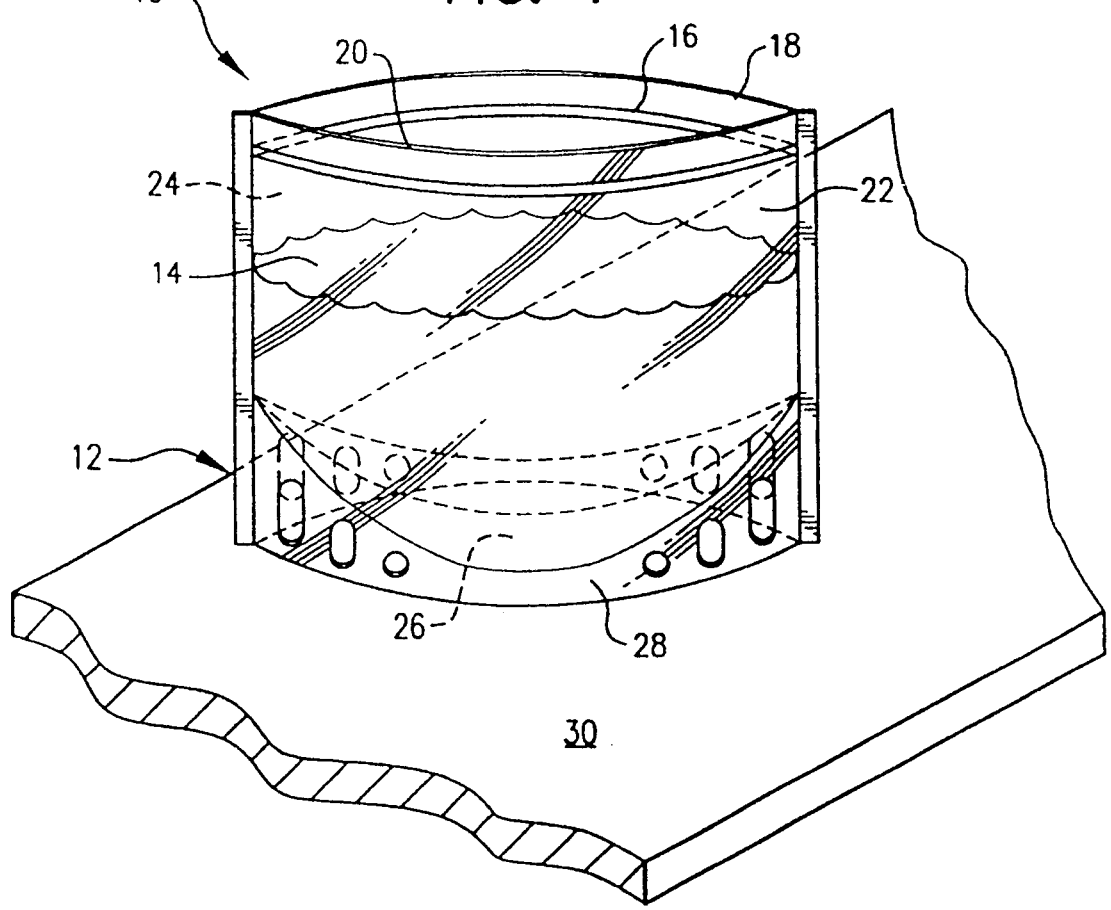
FIG. 1 is a pictorial view of a gusseted pouch constructed in accordance with the invention.

Referring to the drawings, and first to FIG. 1, shown generally at 10 is a gusseted bag or pouch that is designed for use in conjunction with the invention. The pouch 10 has a gusseted base 12 which enables it to stand alone in vertical orientation when it is filled with a liquid medium 14. A person skilled in the art would be familiar as to how the bag is made. However, for the purpose of using it in the method described below, the pouch 10 must be made of a material that is resistant to puncturing, substantially rigid to stand alone in a vertical position, suitably transparent to allow visual inspection of the contents, and has a long shelf life. Preferably, the pouch 10 is comprised of two sheets of thin film, transparent plastic sheets 22 and 24, that lay one on top of the other when the pouch 10 is not filled. The lower portion or region 28 of the sheets 22 and 24 are connected together and closed to form the gusseted base 12. The side edges of the sheets are bonded directly to each other without a gusset, in the manner shown in FIGS. 1 and 8, such that the pouch 10 is a "two-sided" pouch and will lay flat, one sheet on top of the other. The upper portion of the pouch 10, near the edges 18 and 20 of the sheets 22 and 24, are bonded together in a manner that will be described later below.

Various types of suitable bag materials are available from a number of sources. The pouch 10 should be made of laminated plastic films. Suitable materials are available from Riley & Geehr in Evanston, Ill., identified by the following product numbers: DF#400 (Product No. from Riley & Geehr) 48 gauge (0.00048 inches) PET/Adhesive/2.5 gauge LLDPE (overall thickness is 3.1 mil); DF#512 (Product No. from Riley & Geehr), 60 gauge Nylon/Adhesive/3.5 gauge LLDPE (overall thickness is 4.1 mil); DF#300 (Product No. from Riley & Geehr), 72 gauge NylonPVDC/Adhesive/3.5 gauge LLDPE (overall thickness is 4.35 mil).

The pouch 10 is sealed by a "zip-lock" closure, indicated generally at 16. A person skilled in the art would be familiar with the way this type of closure works. In the alternative, the pouch 10 could be sealed by rolling its upper edges 18, 20 together and clipping the rolled portion with a spring clamp. This is not shown in the drawings, however.

Figure 8:
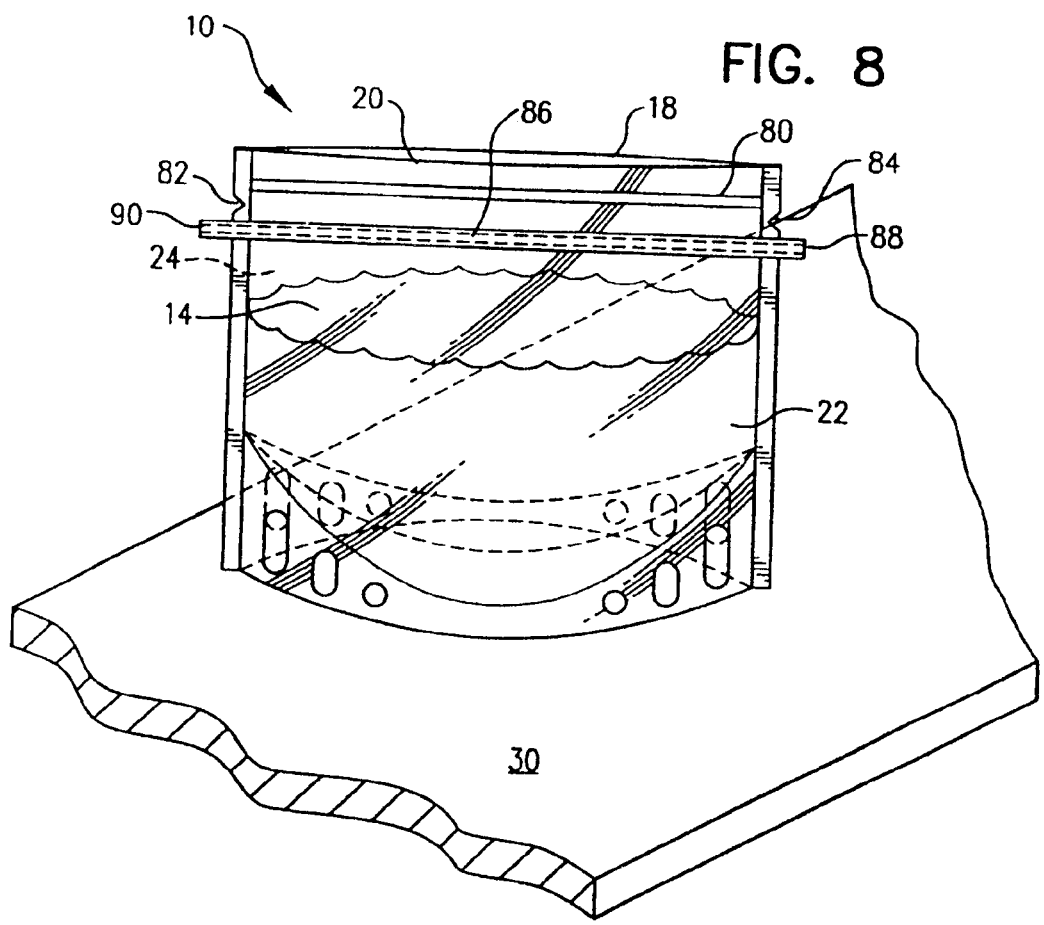
FIG. 8 is a view like FIGS. 1 and 7, but shows a closure wire for the gusseted pouch.

An alternative method of sealing the pouch 10 after the culture medium 14 has been added is shown in FIG. 8, and involves simply bonding the upper edges 18, 20 together by heat sealing or the like to form an airtight seal 80. The fashion in which the edges 18, 20 are bonded together to form the seal 80 is known by those skilled in the art. It is not crucial that the seal 80 be located exactly at the edges 18, 20 of the pouch 10—the seal 80 need only be on the upper portion of the pouch 10. What is important is that the seal 80 is airtight.

FIG. 8 also shows notches 82, 84 cut into the edges of the pouch 10, just below the seal 80, to facilitate the tearing open of the bag for adding a culture sample. A flexible closure wire 86 is attached to one of the sheets 22 or 24, below the notches 82, 84. The length of the closure wire 86 exceeds the width of the pouch 10, such that both ends 88, 90 of the closure wire 86 extend past the edges of the pouch 10.

Figure 9:
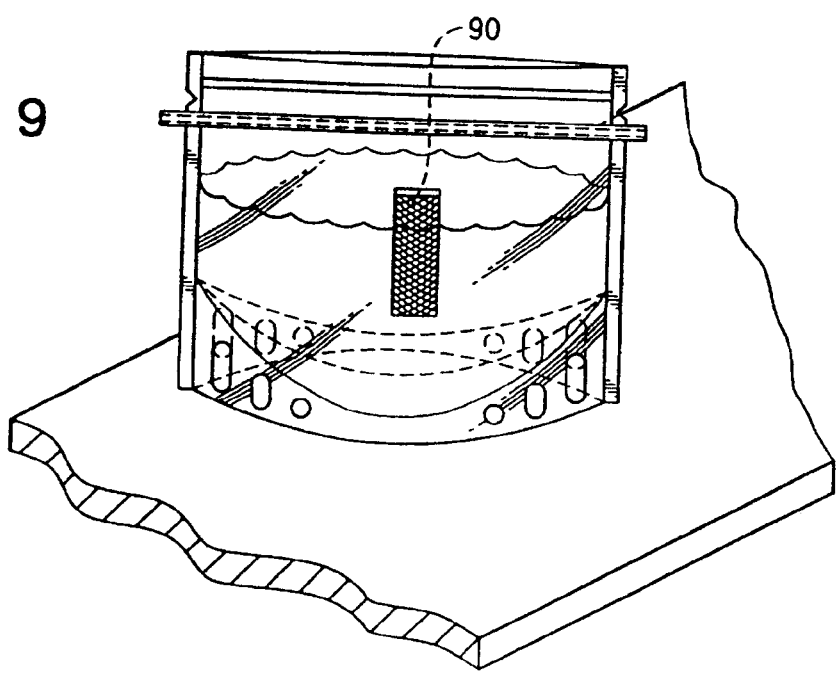
FIG. 9 is a pictorial view like FIG. 8 but shows a pipette sock inside the pouch.
Figure 11:
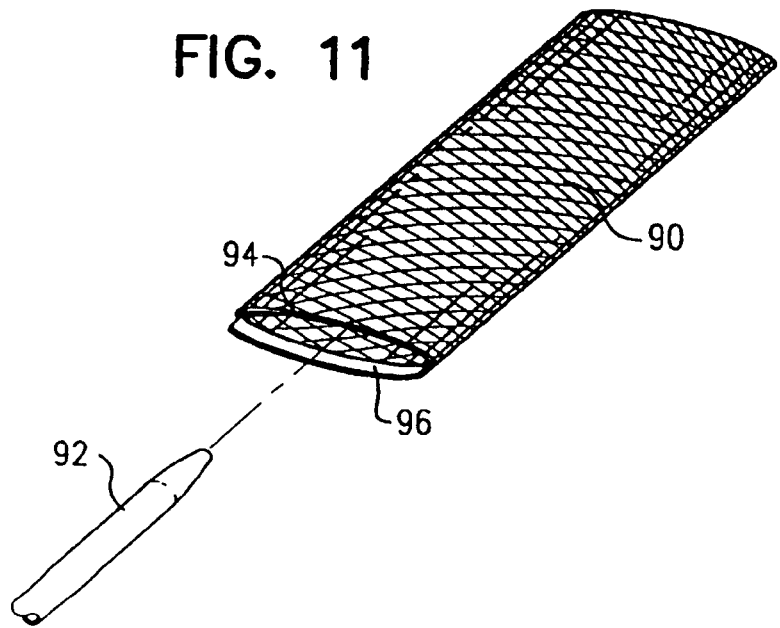
FIG. 11 is a pictorial view of the pipette sock and shows the tapered end of a pipette about the be inserted into an upper opening in the sock.

In an alternative embodiment, a pipette sock 90 is attached to one of the inner walls of the pouch 10 (see FIG. 9). The pipette sock 90 is made of a mesh-type cloth or similar material that will enable the medium and microorganisms in the medium to pass through its walls, but at the same time, serves as a filter for particulate matter. For example, in use, a pipette 92 (see FIG. 11) may be inserted into the sock (after the pouch 10 is open, of course) and the medium may be drawn from inside the pipette sock 90. The sock 90 filters the medium.

Figure 10:
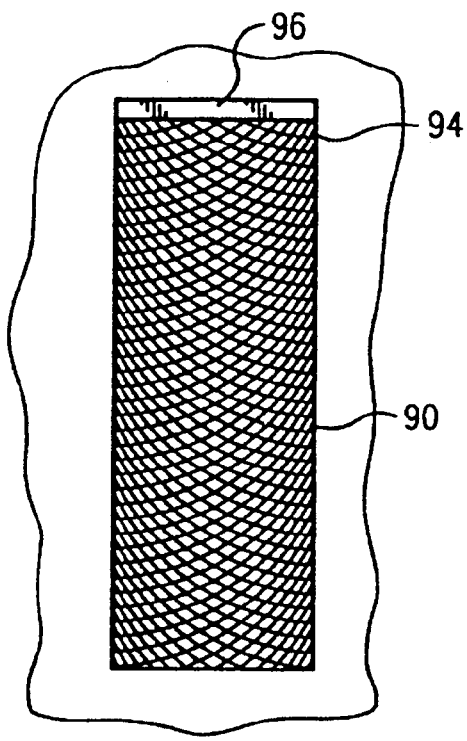
FIG. 10 is an enlarged, fragmented view of the pipette sock shown in FIG. 9.

An upper end 94 of the sock is open for receiving the pipette 92. The lower end is closed. The sock 90 is sealed at 96 to the pouch 10 (see FIG. 10). Any material suitable for use as a filtration medium in the context just described may be used as a pipette sock 90.

When filled, the liquid culture medium 14 applies outward pressure to opposite sides 22, 24 of the pouch 10. This forces sides 22, 24 away from each other. At the base 12 of the pouch 10, the bottom or gusset 26 unfolds. The gusset 26 both defines the floor of a liquid holding vessel and constain the outward movement of sides 22, 24. The lower side edges 28 are stiffened by the opening of the gusset 26 and define a stable base that enables the pouch 10 to rest on any flat surface 30 in the vertical arrangement shown in FIG. 1. When the pouch 10 is closed, it is easy to move from place to place and can be placed on shelves or in boxes along with other pouches of the same construction.

Figure 2:
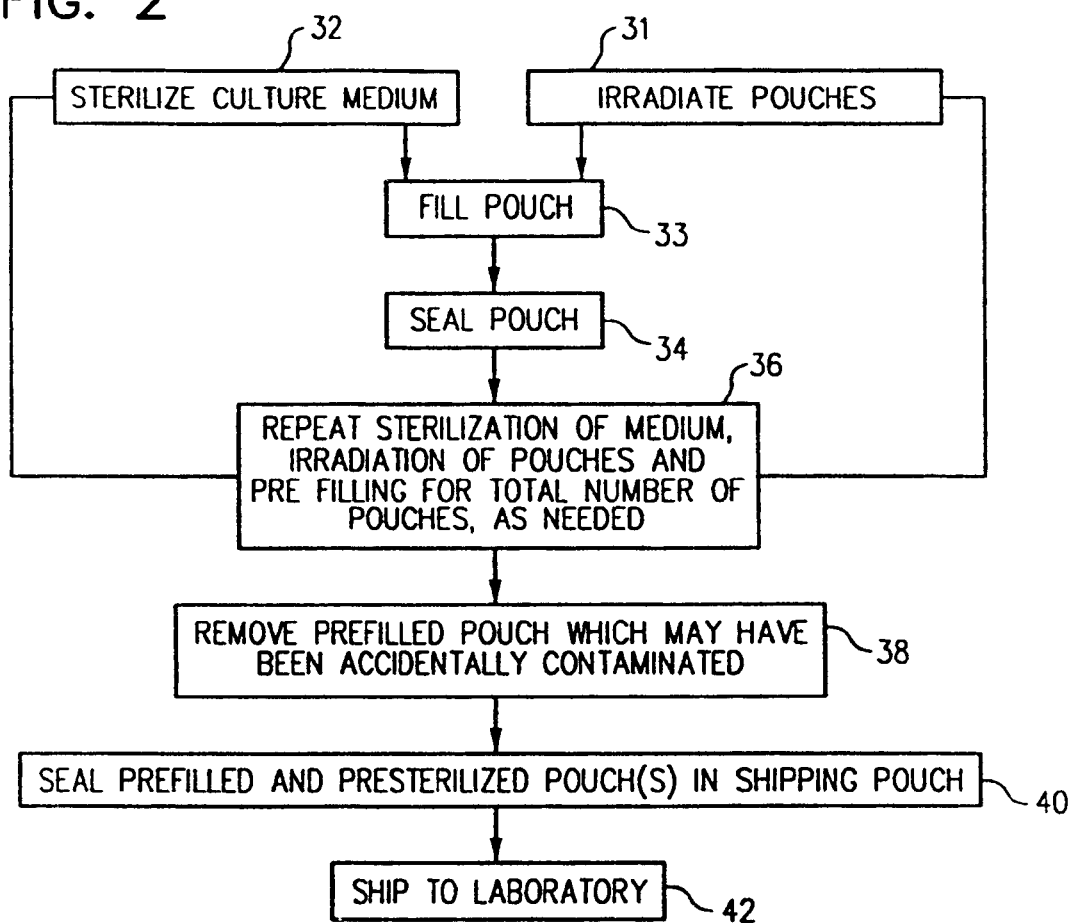
FIG. 2 is the first in a series of two flow charts outlining the various steps of the invention.
Figure 3:
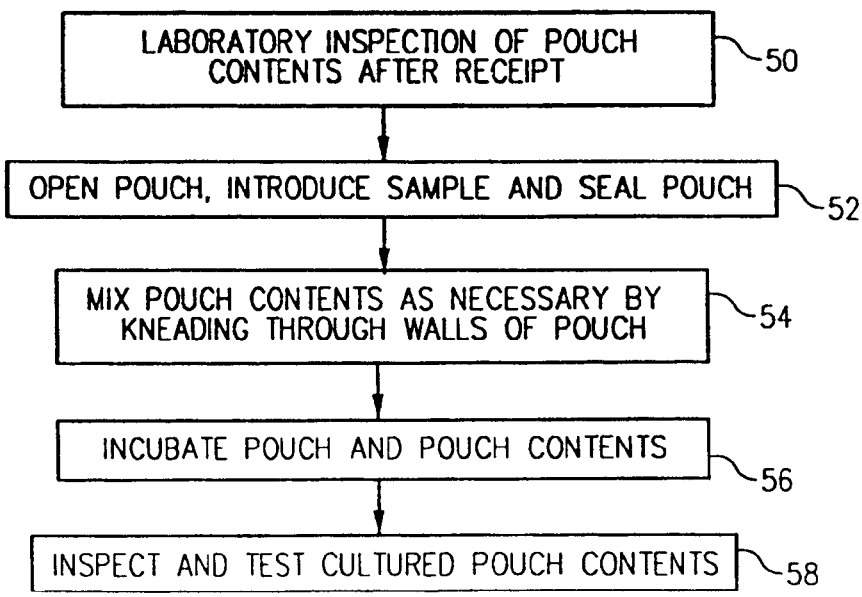
FIG. 3 is the second in a series of two flow charts outlining the various steps of the invention.

In accordance with what is considered to be the invention here, and directing attention now to FIGS. 2 and 3, the pouch 10 is first sterilized by irradiation. Irradiation is a conventional procedure that would be familiar to the skilled person. Irradiation of the pouch 10 is necessary because it is unlikely the materials used to make the pouch can withstand autoclave conditions.

In a parallel step (see 32 in FIG. 1), the culture medium is separately sterilized in an autoclave. Typical autoclave conditions for sterilizing the culture medium involves subjecting the medium to a temperature of 121° C., a pressure of 15 p.s.i., and 100% steam.

The culture medium may consist of any one of a number of conventional formulations used for culturing samples, such as Nutrient Broth, Soybean Casein Digest Broth, Thioglycollate Broth, and Brain Heart Infusion Broth. It is typically known as a culture "broth," which would be understood by a person skilled in the art.

Sterilization of the pouch 10 and culture medium will occur in a clean room under stringent conditions. As indicated at 31, the sterilized medium is placed in the pouch 10, as indicated at 33. Depending on market demand, any number of pouches will be filled with various types of culture media. The pouches are sealed (see 34) and the process is repeated as many times as needed to supply market demand. This is schematically indicated at 36 in FIG. 2.

In the summary of the invention, an alternative embodiment was described involving subjecting a non-sterile culture broth to a non-sterile bag and then subjecting both items to a radiation treatment as a single unit. It is believed gamma rays or electron radiation will render the unit sterile in this situation if applied properly.

If the unit is processed in this way, it is critical that any microorganisms not be allowed to grow to significant levels prior to the radiation treatment. If the growth of the contaminants is not restricted beforehand, then the radiation dosage may not be adequate to completely kill these microorganisms. Also, if the contaminants grow to high levels prior to sterilization, even though the radiation treatment may subsequently kill them all, their presterilization use of critical nutrients (e.g., proteins, amino acids, vitamins, sugars, oxygen) in the medium could result in an inability of the medium to subsequently support the growth of microorganisms when subsequently used for culturing. Moreover, excessive growth of these organisms prior to sterilization may result in the creation and accumulation of toxic waste products that will not be removed by sterilization, but may nevertheless restrict or prevent the growth of microorganisms during culturing. Control of the presterilization growth of the contaminants is accomplished by sterilizing within a short period of time after filling (e.g., 48 hours) or by refrigerating to restrict the growth of the contaminant microorganisms.

Radiation dosage required for sterilization, regardless of which embodiment is used, needs to be determined by experience and may vary depending on pouch material and type of culture medium. Based on current data, a gamma radiation dose of 2.5 Mrads should be sufficient to kill microorganisms with an adequate safety factor.

It has recently been found that this alternative embodiment may now be preferred. Gamma radiation in the range of 15 to 30 kGy is currently in use.

After prefilling and sterilization, the pouches are quarantined for a period of time. Quarantine will reveal any contamination in the pouches and enable culling out unusable pouch and media units prior to laboratory shipment (see 38 in FIG. 2). Quarantine may not be necessary for units that are sterilized together by gamma or electron beam treatment.

Figure 4:
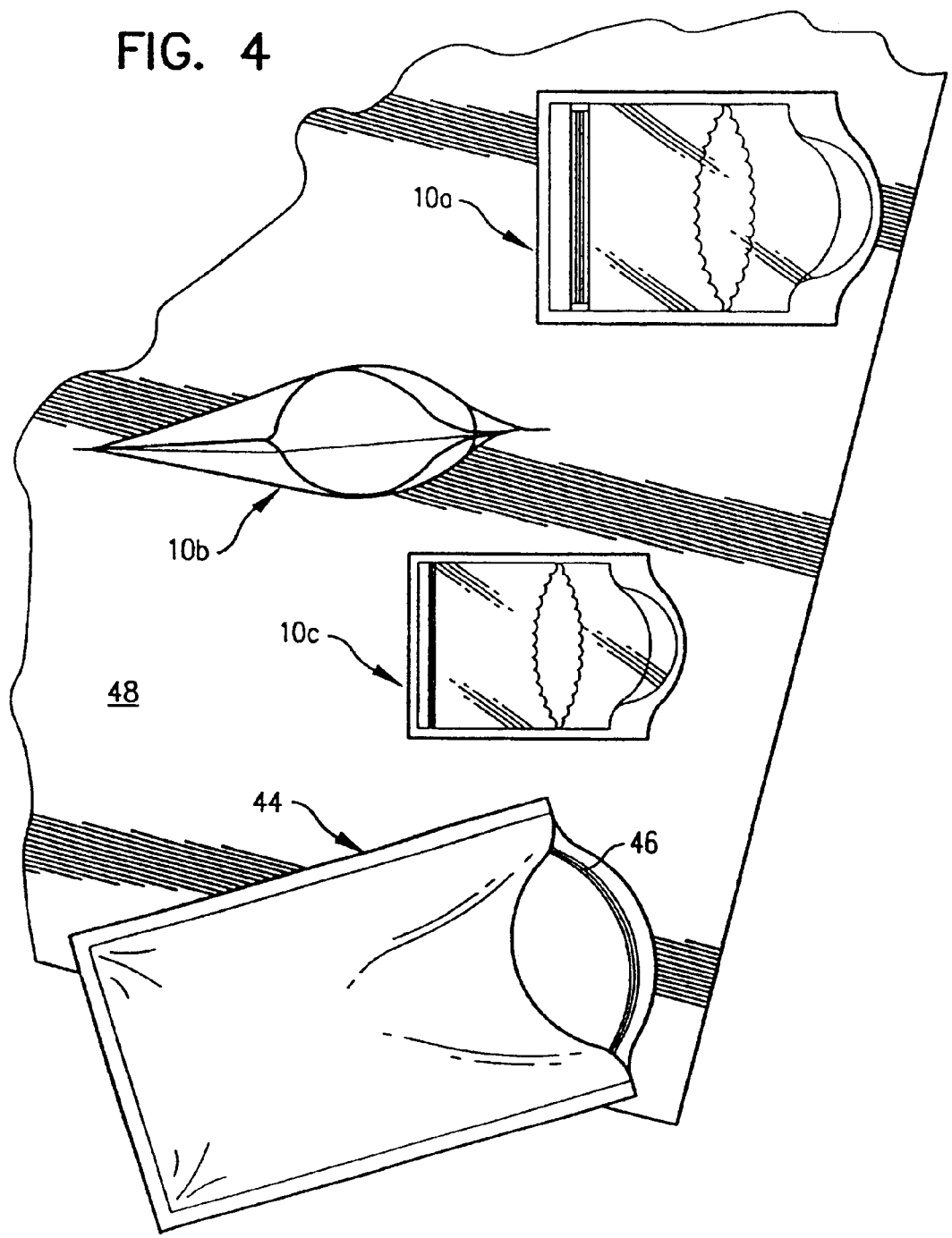
FIG. 4 is a pictorial view of a plurality of gusseted pouches about to be placed in a shipping pouch.

When a laboratory places an order, one or more prefilled and presterilized pouch units are placed in a shipping pouch and sent to the laboratory (see 40 and 42, respectively). Directing attention briefly to FIG. 4, each prefilled pouch 10A, B, C is placed within a foil shipping pouch 44. The shipping pouch 44 is preferably made of DF#505 (Product No. from Riley & Geehr). This material is 48 gauge chemically-treated polyester (provides rigidity). It has a sealing layer of low density polyethylene and an aluminum foil barrier. Like the pouch 10, it has a zip-lock closure 46 which provides a double-seal against leakage or moisture escape from each pouch 10A–C placed in the shipping pouch 44. In FIG. 4, pouches 10A, C are shown lying on their sides on a flat surface 46. Pouch B is standing vertically in the same way as shown in FIG. 1.

Referring now to FIG. 3, as shown at 50, the laboratory receives a shipping pouch 44, opens it, and is able to visually inspect pouch contents immediately. Oftentimes, a visual inspection will reveal microorganism growth in the pouch which means that its contents somehow became contaminated despite the earlier quarantine step. If the visual inspection indicates no abnormalities, then the pouch 10 is used to culture a sample.

Culturing is accomplished by opening pouch 10, introducing a culture sample, and thereafter sealing the pouch (see 52). In some cases, it is necessary to mix pouch contents. This may be a function of the type of sample being cultured. In any event, if mixing is required, it is a simple matter to knead the pouch contents through the flexible walls of the pouch 10 (see 54). In some instances, a mesh bag is placed inside the gusseted bag (see FIG. 7). The purpose of this mesh bag is to filter particles so that if a serological pipette is used to remove bag contents, the pipette will not become clogged. After thorough mixing, the pouch and its contents are placed in an incubator (see 56).

Figure 7:
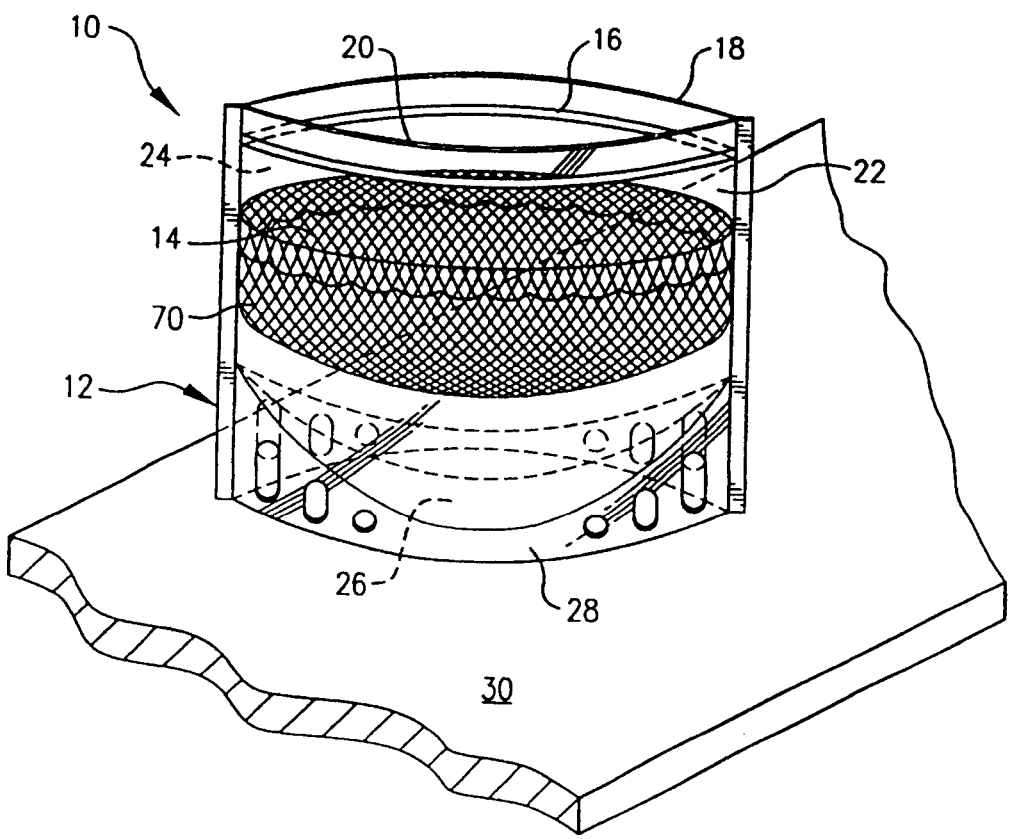
FIG. 7 is a view like FIG. 1 but shows an alternative embodiment of the gusseted pouch.

A "zip-lock" closure for the pouch 10, such as that shown in FIGS. 1 and 7, allows for convenient opening and resealing of the pouch when adding a culture sample to the medium 14. An alternate and probably preferred method involves use of the closure wire 86, previously described above and shown in FIG. 8. To add a sample, the pouch 10 is cut open with scissors or torn open by applying the requisite force at one of the notches 82 or 84 to tear and spread apart the sheets 22 and 24. The sample can be added to the culture medium 14 after the opening has been torn to a sufficient size. To reseal the pouch 10 after the sample has been added, the top edges 18, 20 of the pouch, including the opening that was created, are flattened together and then rolled about the closure wire 86. The ends 88, 90 of the closure wire are then wrapped over the rolled portion to prevent that portion from unrolling (not shown in the drawings).

Figure 5:
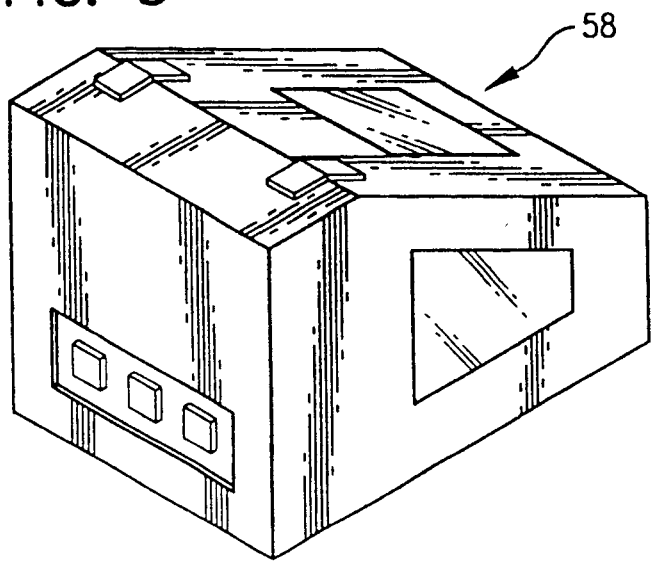
FIG. 5 is a pictorial view of an incubator.
Figure 6:
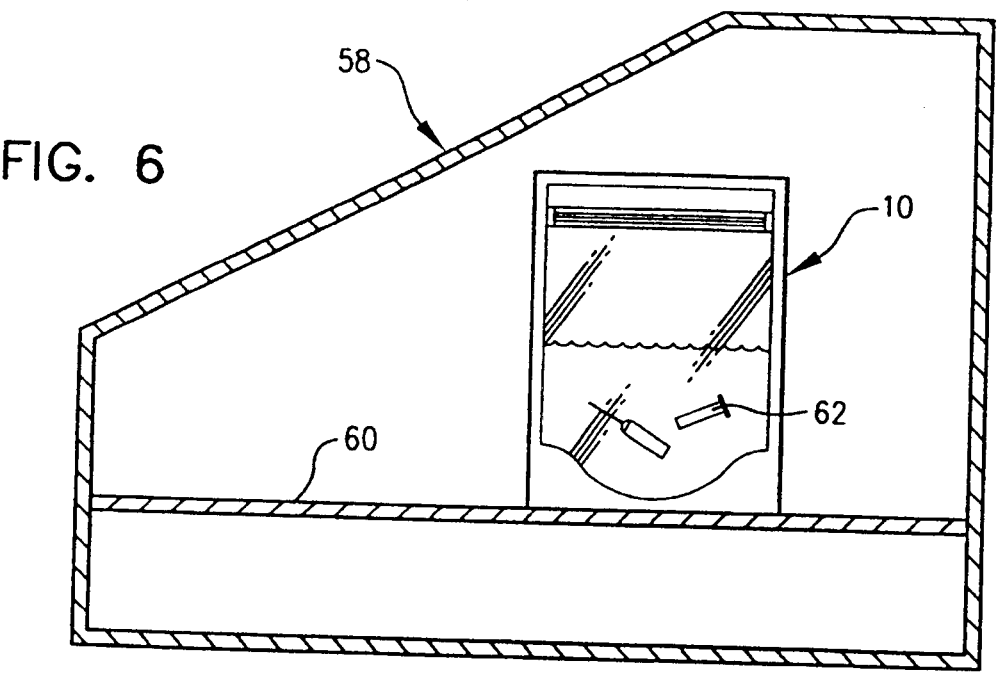
FIG. 6 is a side cross-sectional view of the incubator shown in FIG. 5.

Referring now to FIGS. 5 and 6, incubation conditions depend on culture sample type. An incubator 58 is pictorially shown in FIG. 5. A pouch 10 constructed according to the above description is shown sitting on a horizontal shelf 60 within the incubator 58. The pouch 10 is shown holding a medical syringe and needle 62. In this case, the syringe and needle 62 are being cultured to determine whether it is contaminated.

After incubation, it is a simple matter to inspect the cultured sample and conduct any additional testing required (see 58 in FIG. 3).

When using pouches like the ones disclosed here, it is possible to store prefilled and presterilized pouches more than twelve months prior to shipment or use. The following examples are provided to further illustrate specific embodiments of the method:

EXAMPLE 1

A sterile, flexible, stand-up pouch is prefilled with 225 ml of sterile Buffered Peptone Water for growing Salmonella bacteria as part of method for detecting this organism in a 25 gram food sample. The prefilled pouch is opened, 25 grams of sample is added, and the pouch is resealed by closing the ziplock. If a particulate sample is being analyzed, the pouch is placed in a blender with reciprocating paddles and blended for 1 minute. The pouch is then incubated at 350° C. for 24 hours (+/2 hours). Following incubation, aliquots of the growth medium are removed and analyzed using a rapid methods procedure such as an enzyme immunoassay, a gene probe detection method, or by a traditional pure culture method as described in the Bacteriological Analytical Manual (FDA, 8th Ed.).

By starting with a different liquid culture medium in the stand-up pouch, 25 gram samples can be assayed for different pathogenic bacteria such as *E. coli* 0157, *Staphylococcus aureus,* Listeria spp., and Campylobacter spp.

EXAMPLE 2

A sterile, flexible, plastic bag is prefilled with 375 ml of sterile Buffered Peptone Water for growing Salmonella bacteria as part of a method for detecting this organism in a 375 gram composite food sample. The prefilled bag is opened, 375 grams of sample added, and resealed by rolling down the bag at the opening and sealing with a clip. If a particulate sample is being analyzed, the prefilled, bag is placed in a blender with reciprocating paddles and blended for 1 minute by battering the sides of the bag with the paddles. If the prefilled bag is an ordinary bag without the stand up, gusseted feature, then it is placed in a wire rack for holding the bag in a stand-up position and incubated at 35° C. for 24 hours (+/−2 hours). Following incubation, aliquots of the growth medium are removed and analyzed using a rapid methods procedure such as an enzyme immunoassay, a gene probe detection method, or by a traditional pure culture method as described in manuals such as the Bacteriological Analytical Manual (FDA, 8th Ed.).

EXAMPLE 3

Sterility testing of aseptically packaged foods, pharmaceutical products (e.g., injectable solutions, vaccines), and sterile medical devices (such as needles, catheters, etc.) can be accomplished by adding a sample into sterility testing media such as sterile Tryp Soy Broth or sterile Thioglycollate Broth in a flexible stand-up pouch. With the food, pharmaceutical, and cosmetic samples, a 10 gram sample is added to 100 ml of Tryp Soy Broth and/or 100 ml of Thioglycollate Broth. If the sample is particulate in nature, the pouch is placed in a reciprocating paddle blender for 1 minute to homogenize the sample. The pouch with sample is incubated at 35° C. for 5–7 days and observed for cloudiness in the medium. Objects such as catheters can be added directly into the pouch containing the sterility broths without blending before incubation. Objects that are soft and porous (e.g., gauze, sponges) may benefit from blending with a reciprocating paddle machine.

EXAMPLE 4

Coliform testing of water and wastewater samples is accomplished by adding 100 ml of sample to a pouch containing a nutrient medium supplemented with the reagent o-nitropbenyl β-Dgalactopyranoside (ONPG). The medium may be made as a concentrate such that the addition of the water brings the constituents up to the correct final. concentrations. Alternatively, the medium may be supplied as a powder which is reconstituted to the correct final constituent concentrations with the addition of water. The sample is incubated in the pouch at 35° C. for 24 hours. If coliform bacteria are present, the colorless ONPG compound is converted to a yellow color.

EXAMPLE 5

*E. coli* testing of water and wastewater samples is accomplished by adding 100 ml of sample to a pouch containing a nutrient medium (e.g., lauryl sulfate broth) supplemented with the reagent 4-methylumbelliferyl-β-D-glucuronide (MUG). The medium may be made as a concentrate such that the addition of the water brings the constituents up to the correct final concentrations. Alternatively, the medium may be supplied as a powder which is reconstituted to the correct final constituent concentrations with the addition of water. The sample is incubated in the pouch at 35° C. for 24 hours. If *E. coli* bacteria are present, the colorless MUG compound is converted to a fluorescent bluish compound that is observed under long wave (365 mm) ultraviolet light.

EXAMPLE 6

Environmental surface samples, such as floors, drains, and equipment in a food company plant, are analyzed for the presence of microorganisms such as *E. coli,* Listeria spp., and Salmonella. These samples are collected using sterile swabs or sponges. Swabs or sponges can be added to a flexible stand-up pouch containing 100 ml of lauryl sulfate broth with MUG (for *E. coli*), UJVM broth (for Listeria), or Buffered Peptone Water (for Salmonella). The broth with the swab or sponge is incubated for-18–24 hours at 35° C. After incubation, the liquid culture medium is observed for the presence of bluish fluorescent material under long wave (354 mm) ultraviolet light for the *E. coli* test, or aliquots of the growth medium are removed and analyzed using a rapid methods procedure such as an enzyme immunoassay, a gene probe detection method, or by a traditional pure culture method as described in manuals such as the Bacteriological Analytical Manual (FDA, 8th Ed.) for Listeria and Salmonella testing.

EXAMPLE 7

Fifty grams of food sample such as meat is added to a flexible, plastic bag which incorporates a plastic mesh bag and is prefilled with 450 ml of sterile Butterfield's Phosphate Buffer. With even distribution of the sample, this dilutes the meat 1:10. The pouch is placed into a machine with reciprocating paddles and blended for 1 minute. A one ml aliquot is removed from the pouch using a serological pipette by accessing the diluent on the opposing side of the mesh bag from the meat. This minimizes the possibility of particulates clogging the serological pipette. A quantitative analysis is performed using a pour or spread plate procedure or using a most probable number (MPN) procedure.

With respect to Example 7 above, and referring to FIG. 7, reference numeral 70 illustrates a mesh bag inserted into the gusseted bag. The top ends of the mesh bag extend above the surface of the culture medium, and the bottom of the mesh bag extends towards the bottom of the gusseted bag to a sufficient depth. As mentioned in the preceding paragraph, samples are then introduced into the mesh bag and homogenized. The aliquot, is a sample which is then removed from under the mesh 70 and is cultured in a manner other than incubation. The "pour" or "spread plate" procedures described in the samples would be familiar to a person skilled in the art.

Alternatively, the gusseted bag 10, mesh bag 70, culture medium 14, and sample can all be incubated together, and afterwards, an aliquot is removed by a pipette to perform tests for pathogenic organisms.

Having described the invention, it is to-be understood that its scope is not to be limited by the specific embodiments disclosed above. While seven examples are described, it is not intended that the invention be limited to the examples. In some cases, it may be desirable to use non-gusseted pouches to practice the procedure described above.

The scope of the invention is to be limited only by the patent claims which follow, the interpretation of which is to be made in accordance with the standard doctrines of patent claim interpretation. Claim terms are to be interpreted first in accordance with their plain and ordinary meaning. Dictionary definitions will be suitable to explain claim terms unless expressly indicated otherwise, in some cases, dictionaries set forth more than one definition for the same word. In such case, applicant intends that the broadest definition be applied. In some cases, the claims use terms or expressions like "presterilizing the medium and a flexible stand-up plastic bag," followed by a separate clause which reads "prefilling the bag with the medium." It is specifically intended that this expression covers both instances where the two items are either sterilized separately or together at the same time.

What is claimed is:

1. A prefilled culture medium bag, comprising:

a culture medium; and a bag adapted to contain the culture medium, the bag comprising a pair of thin film plastic sheets, a lower region of the sheets being connected together and closed by a gusset, side edges of the sheets being bonded directly to each other without the use of a gusset so that the upper regions of the sheet may lay flat, one on top of the other, when the bag is either filled or not filled with the culture medium, and wherein an upper region of one sheet may be spread apart from the upper region of the other sheet in order to introduce the culture sample into the bag, and including a closure wire connected to the upper region of one of the sheets, the closure wire having a length that exceeds the width of the bag, in a manner so that the upper regions of the sheets may be rolled around the closure wire to reseal the bag after the culture sample is introduced.

2. The bag of claim 1, wherein the upper regions of the plastic sheets are bonded together to form an airtight seal above the closure wire.

3. The bag of claim 2, further comprising a pair of notches to facilitate the spreading apart of the sheets, the notches being located on the side edges of the sheets between the airtight seal and the closure wire.

4. The bag of claim 2 wherein the sheets are transparent.

5. A prefilled culture medium bag, comprising:

a culture medium; and a bag adapted to contain the culture medium, the bag comprising a pair of thin film plastic sheets, a lower region of the sheets being connected together and closed by a gusset, with side edges of the sheets being bonded directly to each other without the use of a gusset so that the upper regions of the sheets may lay flat, one on top of the other, when the bag is either filled or not filled with the culture medium, and wherein an upper region of each sheet may be spread apart from the upper region, and including a resealable closure located at the upper region of the sheets.

6. The bag of claim 5, including a filter sock located inside the bag.

* * * * *

UNITED STATES PATENT AND TRADEMARK OFFICE
CERTIFICATE OF CORRECTION

PATENT NO. : 6,379,949 B1
DATED : April 30, 2002
INVENTOR(S) : N.R. Ward

It is certified that error appears in the above-identified patent and that said Letters Patent is hereby corrected as shown below:

<u>Title page, Item [54] and Column 1, lines 1-2,</u>
Title, "PREFILLED FLEXIBLE CONTAINERS FOR CULTURING MICROORGANISMS" should read -- PREFILLED CULTURE MEDIUM BAG --

Item [56], References Cited, U.S. PATENT DOCUMENTS, "5,787,428" should read -- 5,785,428 --

OTHER PUBLICATIONS, "1983 Avstract Enclosed." should read -- 1983. --

Signed and Sealed this

Fifth Day of November, 2002

*Attest:*

*Attesting Officer*

JAMES E. ROGAN
*Director of the United States Patent and Trademark Office*